US006582369B1

(12) United States Patent
Huang et al.

(10) Patent No.: US 6,582,369 B1

(45) Date of Patent: Jun. 24, 2003

(54) METHOD FOR DYNAMIC FOCUS CONTROL

(75) Inventors: Jing-Jung Huang, Taipei (TW); Pai-Chi Li, Taipei (TW)

(73) Assignee: Computed Ultrasound Global Corporation, Taipei Hsien (TW)

( * ) Notice: Subject to any disclaimer, the term of this patent is extended or adjusted under 35 U.S.C. 154(b) by 30 days.

(21) Appl. No.: 10/037,100

(22) Filed: Jan. 2, 2002

(51) Int. Cl.[7] .................................................. A61B 8/00

(52) U.S. Cl. ....................................................... 600/447

(58) Field of Search ................................ 600/437, 443, 600/447; 128/916; 73/626, 628; 367/122, 123, 103–105

(56) References Cited

U.S. PATENT DOCUMENTS 4,688,045 A * 8/1987 Knudsen ..................... 343/377
4,949,259 A * 8/1990 Hunt et al. .................... 73/626
4,969,132 A * 11/1990 Reed .......................... 367/122
5,130,717 A * 7/1992 Ewen et al. ................ 343/378
5,522,391 A * 6/1996 Beaudin et al. ............. 600/443
5,724,972 A * 3/1998 Petrofsky ..................... 600/447
5,784,336 A * 7/1998 Gopinathan et al. ........ 367/123
5,935,070 A * 8/1999 Dolazza et al. ............. 600/443
6,168,564 B1 * 1/2001 Teo ............................ 600/443

* cited by examiner

*Primary Examiner*—Francis J. Jaworski

(74) *Attorney, Agent, or Firm*—Alston & Bird LLP

(57) ABSTRACT

Methods perform dynamic focusing of a coherent array imaging system are invented. Dynamic focusing in ultrasonic array imaging involves extensive real-time computations and data communication. Particularly for real-time three-dimensional imaging using fully-sampled two-dimensional arrays, implementation of dynamic focusing can be extremely complicated. The invention described in this disclosure greatly simplifies the delay control mechanism by exploiting both spatial and temporal characteristics of the focusing delay patterns. The simplification primarily results from (1) grouping adjacent channels into sub-apertures for the range dependent focusing component, and (2) non-uniform quantization of the delay values.

16 Claims, 7 Drawing Sheets

METHOD FOR DYNAMIC FOCUS CONTROL

FIELD OF THE INVENTION

The present invention is related to a method for dynamic focus control, and more particularly to a method that performs dynamic focusing of a coherent array imaging system.

BACKGROUND OF THE INVENTION

Dynamic focusing provides high focusing quality over the entire depth of interest, such as U.S. Pat. No. 5,581,517 and U.S. Pat. No. 5,111,695. In an array imaging system, focusing is typically done by first delaying the backscattered signals based on the propagation path length difference. The delayed signals are then coherently summed across the array. This is also known as the delay-and-sum approach. Since the medical ultrasound imaging primarily works in the near field region, the focusing delay for a particular channel changes as a function of range. Thus, the delay value must be dynamically updated. In other words, the real-time interpolation is required to increase the effective data sampling rate for higher focusing accuracy. Considering the large number of system channels, implementation of dynamic focus control is complicated. The complexity becomes more significant when a fully sampled, two-dimensional array is used. In this case, the number of channels can be as large as several thousands. Thus, efficient dynamic focus control schemes must be developed to reduce the system complexity.

Imaging with two-dimensional arrays has gained broad interest in the past few years. Potential advantages of such a system include reduced slice thickness, improved correction of sound velocity inhomogeneities and real-time three-dimensional imaging. Despite of the potential benefits, two-dimensional arrays have not been widely used in medical ultrasound. Particularly for three-dimensional imaging with two-dimensional (i.e. lateral and elevational) electronic steering, fully sampled arrays are required. The implementation is not possible with current electronic technologies unless major simplification can be achieved without significant image quality degradation.

Dynamic focusing in ultrasonic array imaging involves extensive real-time computations and data communication. Particularly for real-time three-dimensional imaging using fully-sampled two-dimensional arrays, the implementation of dynamic focusing can be extremely complicated.

According to the prior art, the dynamic focusing using arrays was performed without grouping adjacent channels and with uniform delay quantization.

Therefore, conventional approaches control individual channels independently. As the total channel count increases, this becomes impractical. Uniform quantization of delay values also results in a waste in system resources.

SUMMARY OF THE INVENTION

It is therefore a primary objective of the present invention to provide a method for dynamic focus control which describes details of the focus control scheme and demonstrates its efficacy for three-dimensional imaging using two-dimensional arrays. By exploiting characteristics of the range dependent focusing term, complexity is significantly reduced and implementation of dynamic receive focusing becomes much more feasible. Note that although the algorithms are developed for two-dimensional arrays, the same principles can be easily adopted to systems using one-dimensional arrays.

It is another objective of the present invention to provide a method for dynamic focus control which can remove a time waste without sacrificing the focusing quality by grouping adjacent channels and/or non-uniform quantization.

It is further an objective of the present invention to provide a method for dynamic focus control which designs a delay controller for dynamic focusing using arrays.

It is still another object of the present invention to provide a method for dynamic focus control which greatly simplifies the delay control architecture by exploiting characteristics of focusing delay patterns. With the invention, the beam former can be implemented with a substantially low size and cost. Advantages of the invention become more significant when the system channel count is large (e.g., in fully sampled 2D arrays).

It is further a more object of the present invention to provide a method for dynamic focus control which divides the focusing term into a range independent term and a term inversely proportional to the range. Since the second term decreases as the range increases, approximation can be made to simplify the control architecture with the focusing error decreasing as the range increases.

According to the present invention, it is provided a method of dynamic focus control for an array imaging system having an array of channels, each of which has a delay value and a delay controller for performing a delay control. In the method of dynamic focus control is characterized in that the delay value of a particular said channel is divided into a range independent component and a range dependent component, wherein the range dependent compontent is inversely proportional to a range and has a corresponding $\Phi$ value dependent on the location of said channel.

In accordance with the present invention, the array of channels is divided into a plurality of sub-arrays.

In accordance with the present invention, all the channels in a sub-array have a common initial delay parameter $\Phi'$.

In accordance with the present invention, determination of a sub-array geometry is critical in minimizing the focusing error.

Preferably, the array of channels is a one-dimensional array.

Preferably, the array of channels is a two-dimensional array.

Preferably, the two-dimensional array is divided into concentric rings.

Preferably, each of the ring is further divided into smaller segments in order to reduce potential approximation errors for off-center beams, and channels inside a specific segment use a specific common $\Phi'$ value and thus specific delay controller.

Preferably, the $\Phi'$ value is defined as the mean of all the respective $\Phi$ values within the specific segment.

Preferably, the $\Phi$ value is non-uniformly quantized.

Preferably, a number of delay change patterns are quantized via said non-uniform quantization.

Preferably, the delay controller is a multiplexer that is used to select an entry of said delay change pattern.

Preferably, the multiplexer only needs a portion of a delay table.

Preferably, focus quality is finely tuned in range by modifying the initial delay such that the delay error is zero at a reference range.

The foregoing and other features and advantages of the present invention will be more clearly understood through the following descriptions with reference to the drawings, wherein:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

For the sector imaging using a one-dimensional array according to the present invention, the received focusing delay of a channel can be represented as $$t_{rx} = \frac{x\sin\theta}{c} + \frac{1}{R} \times \frac{x^2\cos^2\theta}{2c},$$

where x is the distance between the channel and the array center, c is the sound velocity, θ is the steering angle, and R is range of the focal point. Note that the first term is independent of the range R and is also known as the steering term. The second term is known as the focusing term and is a function of R. For the dynamic focusing, the system focuses along the entire range of interest. Therefore, $t_{rx}$ needs to be constantly updated at every range, every channel and every steering angle.

Let $\Phi=x^2\cos^2\theta$. Since the other term (i.e., $-x\sin\theta/c$) is independent of R and can be specified at the beginning of each beam, the total delays at a range R can then be calculated given the value of Φ. Consequently, given the initial parameters (including $-x\sin\theta/c$ and Φ), the delay controller can effectively perform dynamic focusing at every range R.

Figure 1:
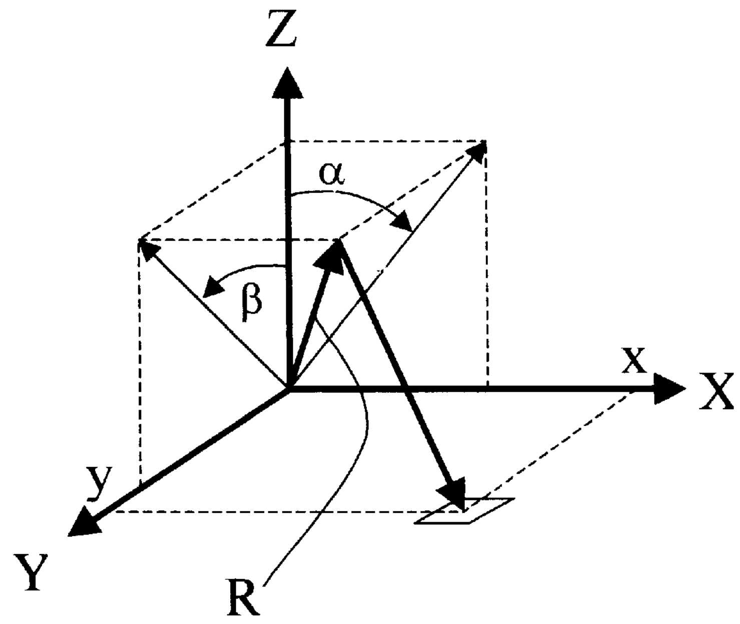
FIG. 1 shows the coordinates of the three-dimensional imaging space according to the present invention, wherein the array is in the x-y plane, z is the depth direction, and α and β are the lateral and elevational steering angles, respectively.

For the three-dimensional imaging using a two-dimensional array, the delay can be derived in a similar fashion.

$$t_{rx} = -\frac{(x\tan\alpha + y\tan\beta)}{c(1+\tan^2\alpha+\tan^2\beta)^{1/2}} + \frac{1}{R} \times \frac{(x^2+y^2)+(x\tan\beta - y\tan\alpha)^2}{2c(1+\tan^2\alpha+\tan^2\beta)},$$

where (x, y) is the coordinate of a particular channel with the array center at position (0,0); α and β are the steering angles along the lateral direction and the elevational direction, respectively. FIG. 1 shows the coordinates. Similar to the one-dimensional case, the formula is also divided into a term independent of range R and a term with R at the denominator. In other words, the following term can be defined:

$$\Phi = \frac{(x^2+y^2)+(x\tan\beta - y\tan\alpha)^2}{1+\tan^2\alpha+\tan^2\beta}.$$

Figure 2:
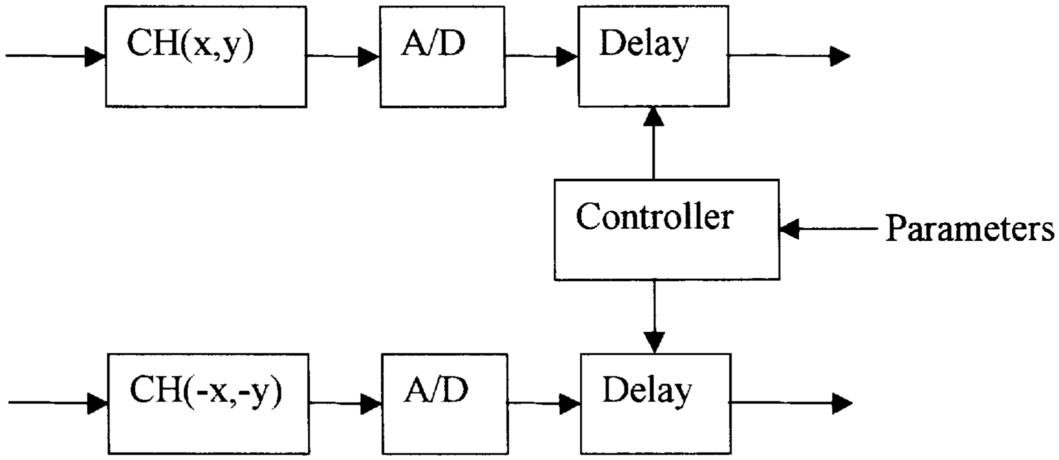
FIG. 2 shows the block diagram based on a direct implementation of the dynamic focusing according to the present invention.

Note that the d) value of channel (x, y) is identical to that of channel (−x, −y). Therefore, for an N-by-N two-dimensional array, the number of delay control units can be reduced to $N^2/2$. FIG. 2 shows the block diagram based on direct implementation of the dynamic focusing. At the beginning of each beam, the initial parameters described previously are sent to each channel. The delay unit in each channel then has to calculate the overall focusing delay at each range. For an N-by-N two-dimensional array with maximum π/4 steering angle in both α and β directions, the number of beams is $2N^2$ assuming the Nyquist spatial sampling. Consequently, the number of initial parameters, which needs to be loaded into the receive beamformer at the beginning of each beam, is $4N^4$ (i.e., $N^2$ channels times $2N^2$ beams times 2 parameters). At a typical N (e.g., 64), this requires a significant amount of data communication. The purpose of this invention is to devise an efficient method such that the total number of Φ can be dramatically reduced.

The simplification scheme keeps the first term unchanged but uses the same Φ for adjacent channels. In other words, the proposed scheme makes certain approximation to the focusing term but maintains the same steering accuracy. Suppose D is approximated by Φ', i.e., $$\Phi' = \Phi + \delta,$$

where δ is the approximation error. Then the approximated total delay $t_{rx}'$ becomes:

$$t_{rx}' = t_{rx} + \frac{\delta}{2Rc},$$

where $t_{rx}$ is the original delay. The last term is a delay error which may cause the image quality degradation. Nonetheless, the delay error decreases as range R increases. Consequently, the image quality degradation occurs only at shallower depths.

The Φ values of neighboring channels are approximated by a single value. In other words, the two-dimensional array is divided into sub-arrays. Determination of the sub-array locations is critical in minimizing the focusing error. One approach is to partition the array into concentric rings. As an example, the number of channels An in a ring can be determined as the following $$\Delta n \leqq \sqrt{(n-0.5)^2 + 16(n-0.5)\epsilon_1 G \times f_{/number}} - (n-0.5),$$

where n is the inner radius of the ring, $\epsilon_1$ is a pre-specified fractional phase error (i.e. delay error times the carrier frequency over $2\pi$); and G is a gain factor defined as $$G = \exp\left[\gamma\left(\frac{n}{n_0} - 1\right)\right],$$

where $n_0$ is the radius of the first (smallest) ring, and $\gamma$ is a parameter for finely tuning the array partition. In general, G can be any function of n over $n_0$ that increases monotonically. This is due to the fact that as more and more channels become active, the delay error can also increase without significantly affecting the image quality because R also increases.

Figure 3:
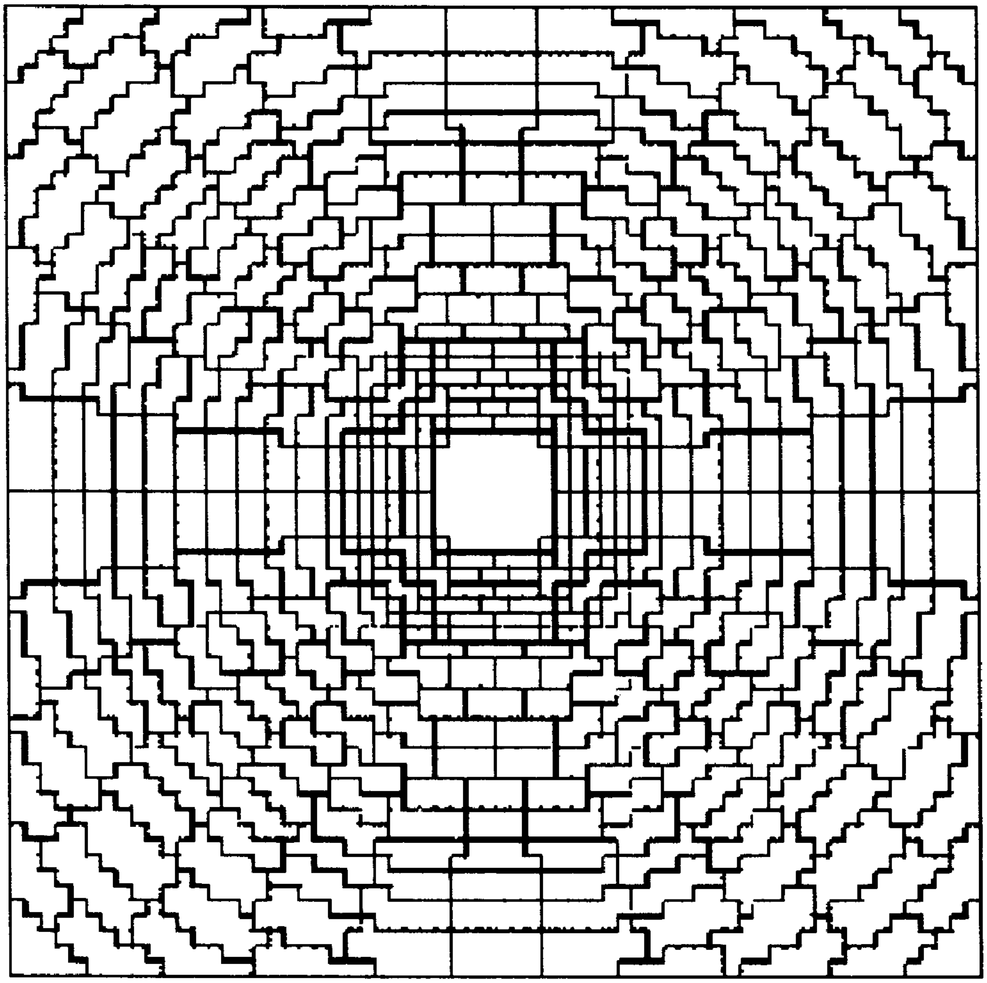
FIG. 3 is a typical segmentation pattern which shows the grouping of adjacent channels according to the present invention.
Figure 4:
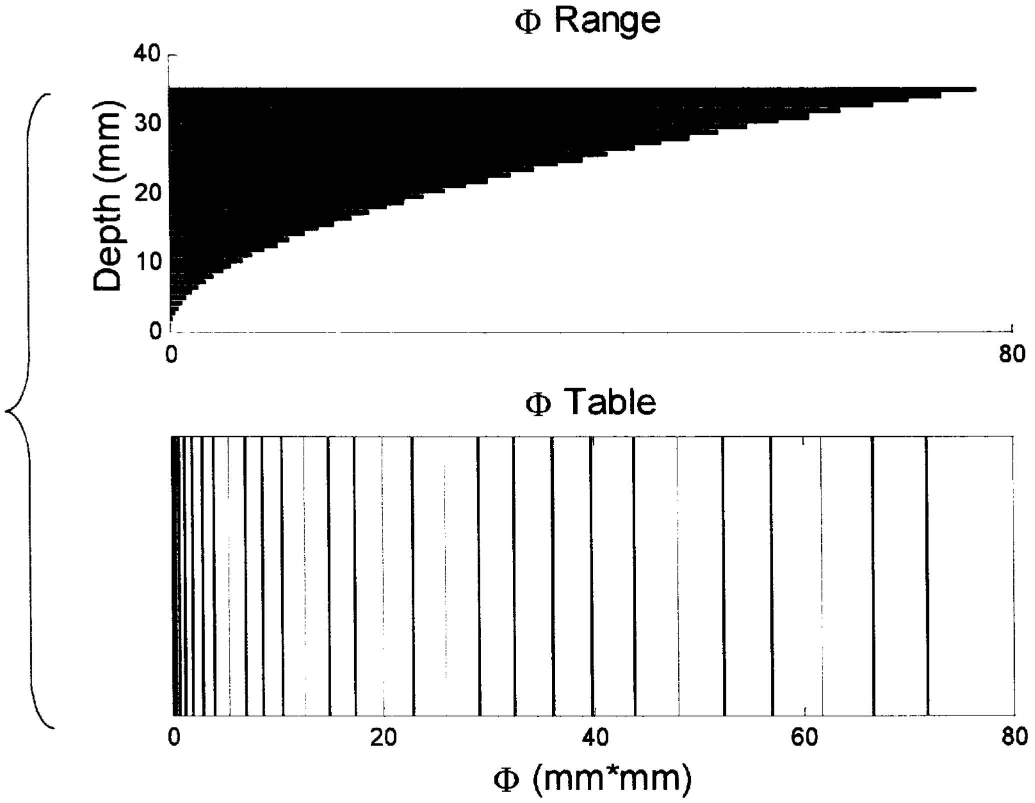
FIG. 4 shows the non-uniform quantization of Φ value according to the present invention.

After determining the radius n, each ring needs to be further partitioned into smaller zones. The angular span of each zone can be defined $$\xi = \frac{M \times \Delta n}{n},$$

where M is a pre-specified aspect ratio. Through this procedure, the array partition can be made. Channels inside the same zone use the same Φ' value and thus, the same delay control unit. The common Φ' value can be defined as the mean of all the Φ values inside the same zone. A typical segmentation pattern is shown in FIG. 3. Let $\epsilon_1$ be 0.05, $n_0$ be 4, $\gamma$ be 0.15, M be 3 and f/number be 2, the 64-by-64 array can be controlled by using only 227 control units. Note that the total number of zones is 454 due to the symmetry in Φ. Also note that an $\epsilon_1$ of 0.05 means that the maximum focusing phase error is 18 degrees (i.e., 0.05*360). 100581 The range of values of Φ is limited since many values are either the same or only slightly different from each other. The range of Φ that is used by all beams at a particular range is shown in the top panel of FIG. 4. Because larger Φ values occur at outside channels, larger quantization error of Φ can be tolerated in this case since these channels do not become active until a relatively large R is reached. In other words, non-uniform quantization of Φ can be used. It can be shown that the number of quantization levels L using non-uniform quantization can be obtained as $$L = \frac{N}{8\sqrt{2} \times \varepsilon_2 \times f_{lnumber}},$$

where $\epsilon_2$ is an error constraint, and the quantized value of Φ is $$\Phi_i = 8\times(\epsilon_2\times\lambda\times f_{1\ number})^2\times(2i^2-2i+1), i\in[1,L],$$

where λ is wavelentgh of the carrier. If a uniform quantizer is used in the same situation, at least $L^2$ levels need to be used to obtain the same level of delay accuracy. Let N be 64, $\epsilon_2$ be 0.1; carrier frequency be 4 MHz and f/number be 2, there are only 28 qunatization levels. Among these, the 28th Φ is never used if the spatial quantization in FIG. 4 is used. Therefore, 27 levels are adequate.

For a given Φ', there is an error exists at all ranges. Further improvement can be achieved by properly choosing a reference range. A modified delay to $t_{rx}''$ can be expressed as the following $$t_{rx}''(R) = t_{rx}'(R) - \frac{\delta}{2R_0c} = t_{rx}(R) + \frac{\delta}{2Rc} - \frac{\delta}{2R_0c}$$

where $R_0$ is the reference range. In other words, $t_{rx}''$ is equal to the ideal value $t_{rx}$ at a range of interest $R_0$. Generally speaking, delay error would become q-times of the original error at R with $$q(R) \equiv \left|\left(\frac{\delta}{2Rc} - \frac{\delta}{2R_0c}\right) \Big/ \frac{\delta}{2Rc}\right| = \frac{|R_0 - R|}{R_0}$$

By properly selecting $R_0$, q can be less than 1, meaning errors are further suppressed.

Figure 5:
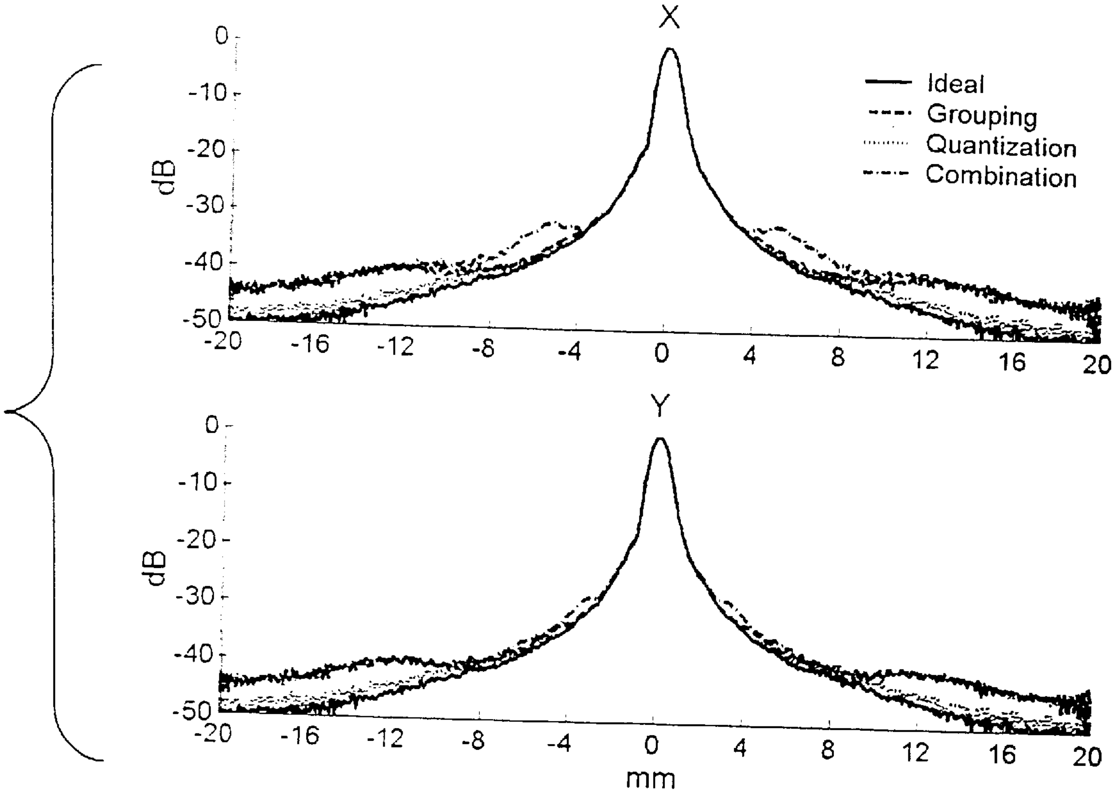
FIG. 5 shows four beam patterns for α=0 degree, β=0 degree, and R=15 mm according to the present invention, wherein the upper is the projection of the beam plots along the x direction and the lower is the projection of the beam plots along the y direction.
Figure 6:
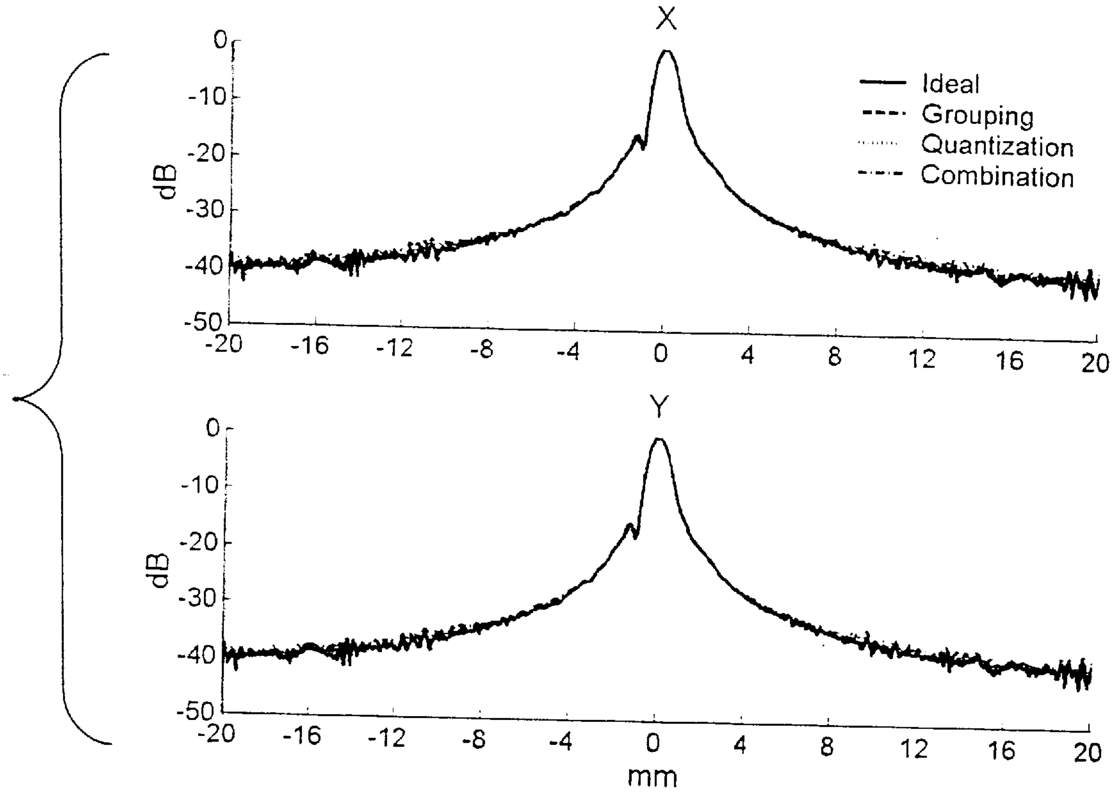
FIG. 6 shows four beam patterns for α=0 degree, β=0 degree, and R=30 mm according to the present invention, wherein the format is the same as that in FIG. 5.

Simulations have been done to demonstrate efficacy of the invention. The simulations are based on the angular spectrum method. FIG. 5 and FIG. 6 show four beam patterns at 15 mm and 30 mm respectively. Each figure shows the projection of the beam plots along the x (upper) and y (lower) directions, wherein the first plot assumes ideal delays with no approximation; the second plot employs the grouping technique shown in FIG. 3; the third plot utilizes the non-uniform quantization scheme shown in FIG. 4; and fourth plot combines both techniques. In the case of 15 mm, sidelobes are elevated due to quantization errors. Nonetheless, the mainlobe width is unchanged and the increase in sidelobe levels is minimal. Considering that 15 mm is shallow for most clinical situations, the degradation is negligible. At 30 mm, the four beam patterns are virtually identical as shown in FIG. 6. Simulated sound fields at non-zero steering angles also have similar results.

Figure 7:
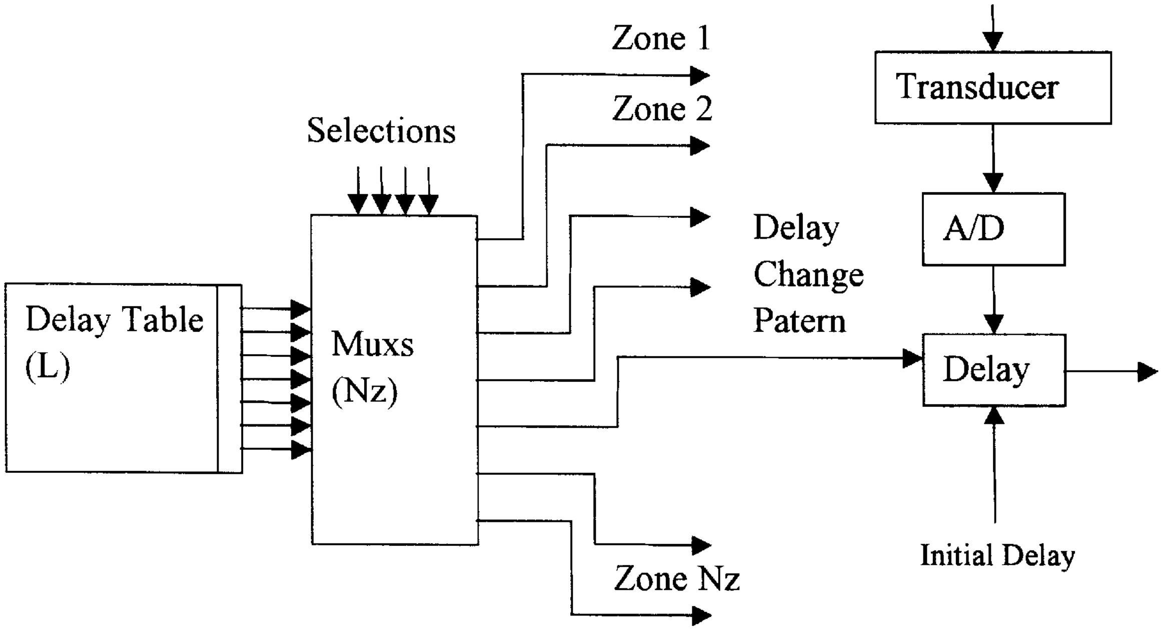
FIG. 7 shows the block diagram of the proposed architecture according to the present invention.
Figure 8:
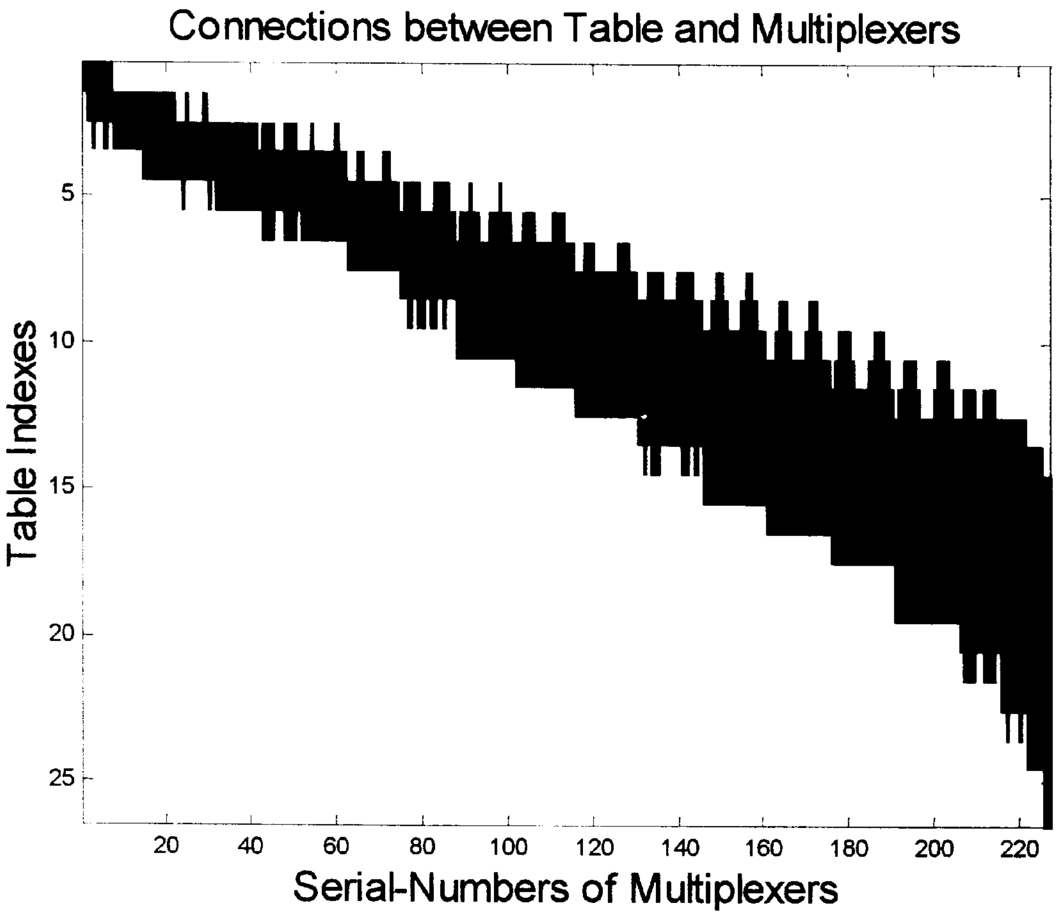
FIG. 8 shows the connections between the table and the multiplexer according to the present invention.

A block diagram of the proposed architecture for the invention is shown in FIG. 7, in which a delay table and a multiplexer are used to implement dynamic focusing control. In addition, the connections between the look-up-table and the multiplexer shown in FIG. 8 reveal that not all connections are used. Thus, the size of the multiplexer can be further reduced. Note that each Φ corresponds to a delay change pattern. The delay change pattern can be a single bit data stream with 1 representing delay change and 0 representing no change. Comparison between the invention and conventional approaches is summarized in table 1.

| | Original | New |
|---|---|---|
| No. of Controllers | 2048 | 227 |
| Control Method | Complex | Simple |
| Controller Size | Large | Small |
| Image Quality | Excellent | Slightly Degradation in the Near Field |
| Initial Delay Table | 32 M-words | 32 M-words |
| Parameter Table | 16 M-words | 1.8 M-words |
| Change-Pattern Table | None | <1 Mb |

Based on the design procedures outlined above, different segmentation schemes can be implemented. The invention can be extended to any field with array focusing in the near-field, not necessarily restricted in the medical ultrasound.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method of dynamic focus control for an array imaging system having an array of channels, each of which has a delay value and a delay controller for performing a delay control, comprising a step of dividing delay value of a particular said channel into a range independent component and a range dependent component, wherein said range dependent component is inversely proportional to a range and has a corresponding Φ value dependent on the location of said channel.

2. The method as claimed in claim 1, wherein said method further comprises a step of dividing said array of channels into a plurality of sub-arrays.

3. The method as claimed in claim 2, wherein all said channels in a specific sub-array have a common initial delay parameter Φ'.

4. The method as claimed in claim 2, wherein determination of a sub-array geometry is critical in minimizing the focusing error.

5. The method as claimed in claim 2, wherein said array of channels is a one-dimensional array.

6. The method as claimed in claim 2, wherein said array of channels is a two-dimensional array.

7. The method as claimed in claim 6, wherein said two-dimensional array is divided into concentric rings.

8. The method as claimed in claim 7, wherein each of said ring is further divided into smaller segments in order to reduce potential approximation errors for off-center beams, and channels inside a specific segment use a specific common Φ' value and thus share a specific delay controller.

9. The method as claimed in claim 8, wherein said Φ' value is defined as the mean of all the respective Φ values within said specific segment.

10. The method as claimed in claim 1, wherein said method further comprises a step of non-uniform quantization of said Φ value.

11. The method as claimed in claim 10, wherein said array of channels is a one-dimensional array.

12. The method as claimed in claim 10, wherein said array of channels is a two-dimensional array.

13. The method as claimed in claim 10, wherein a number of delay change patterns are quantized via said non-uniform quantization.

14. The method as claimed in claim 13, wherein said delay controller is a multiplexer that is used to select an entry of said delay change pattern.

15. The method as claimed in claim 14, wherein said multiplexer only needs a portion of a delay table.

16. The method as claimed in claim 15, wherein focus quality is finely tuned in range by modifying the initial delay such that the delay error is zero at a reference range.

* * * * *